United States Patent
Liang et al.

(10) Patent No.: US 11,521,363 B2
(45) Date of Patent: Dec. 6, 2022

(54) ULTRASONIC DEVICE, AND METHOD AND SYSTEM FOR TRANSFORMING DISPLAY OF THREE-DIMENSIONAL ULTRASONIC IMAGE THEREOF

(71) Applicant: SHENZHEN MINDRAY BIO-MEDICAL ELECTRONICS CO., LTD., Guangdong (CN)

(72) Inventors: Tianzhu Liang, Shenzhen (CN); Yaoxian Zou, Shenzhen (CN); Muqing Lin, Shenzhen (CN); Wenda Gong, Shenzhen (CN); Lei Zhu, Shenzhen (CN); Helin Feng, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 16/612,745

(22) PCT Filed: May 12, 2017

(86) PCT No.: PCT/CN2017/084197
§ 371 (c)(1),
(2) Date: Mar. 6, 2020

(87) PCT Pub. No.: WO2018/205274
PCT Pub. Date: Nov. 15, 2018

(65) Prior Publication Data
US 2020/0202635 A1      Jun. 25, 2020

(51) Int. Cl.
*G06T 15/00* (2011.01)
*G06T 19/20* (2011.01)
(Continued)

(52) U.S. Cl.
CPC ............ *G06T 19/20* (2013.01); *A61B 8/0866* (2013.01); *A61B 8/483* (2013.01); *A61B 8/5207* (2013.01);
(Continued)

(58) Field of Classification Search
CPC ..... A61B 8/483; A61B 8/5207; A61B 8/0866; A61B 8/00; G06T 7/0012;
(Continued)

(56) References Cited

U.S. PATENT DOCUMENTS 8,103,066 B2 *   1/2012   Kim .................... A61B 8/469
                                                        382/128
8,556,814 B2 *  10/2013   Monteiro de Barros Carneiro .....
                                                        G16H 50/20
                                                        706/14
(Continued)

FOREIGN PATENT DOCUMENTS

CN       101035470 A      9/2007
CN       101102721 A      1/2008
(Continued)

OTHER PUBLICATIONS

Anderson R, Stenger B, Wan V, Cipolla R. 2013. Expressive visual text-to-speech using active appearance models. In: Computer Vision and Pattern Recognition (CVPR), 2013 IEEE conference on. Piscataway: IEEE, 3382-3389.*

(Continued)

*Primary Examiner* — Phu K Nguyen
(74) *Attorney, Agent, or Firm* — Sheppard Mullin Richter & Hampton LLP

(57) ABSTRACT

An ultrasonic device and a method and system for transforming the display of a three-dimensional ultrasonic image thereof. The method comprises: first acquiring original ultrasonic three-dimensional body data including a tested object (Continued)

(S10); detecting the orientation of the tested object from the original ultrasonic three-dimensional body data according to image features of the tested object (S20); then comparing the orientation of the tested object with a desired orientation, so as to obtain a rotation transformation parameter in a three-dimensional coordinate system (S30); next, rotating and transforming the original ultrasonic three-dimensional body data according to the rotation transformation parameter, so as to obtain the transformed three-dimensional body data (S40); and finally, outputting the transformed three-dimensional body data (S50). Therefore, the ultrasonic three-dimensional body data of the tested object can automatically rotate to the desired orientation without requiring manual adjustment, thereby improving the efficiency thereof.

17 Claims, 6 Drawing Sheets

(51) Int. Cl.
*A61B 8/08* (2006.01)
*G06T 7/00* (2017.01)

(52) U.S. Cl.
CPC .. *G06T 7/0012* (2013.01); *G06T 2207/10136* (2013.01); *G06T 2207/20081* (2013.01); *G06T 2207/30044* (2013.01); *G06T 2207/30204* (2013.01); *G06T 2210/41* (2013.01); *G06T 2219/2016* (2013.01)

(58) Field of Classification Search
CPC . G06T 2207/30201; G06T 2207/30204; G06T 2207/10136; G06T 2219/2016; G06T 19/20; G06T 2207/20081; G06T 2210/41; G06T 7/73; G06T 2207/30044
USPC ......................................................... 345/418
See application file for complete search history.

(56) References Cited

U.S. PATENT DOCUMENTS

| | | | |
|---|---|---|---|
| 8,591,420 B2 | 11/2013 | Hamada | |
| 8,600,129 B2* | 12/2013 | Seko | G06T 19/00 382/128 |
| 8,617,075 B2* | 12/2013 | Tsujita | A61B 8/4254 600/443 |
| 9,134,420 B2* | 9/2015 | Lee | G06T 19/00 |
| 9,220,482 B2* | 12/2015 | Kim | A61B 8/463 |
| 9,241,685 B2* | 1/2016 | Ajiki | G01S 7/52073 |
| 9,510,804 B2* | 12/2016 | Lee | A61B 8/0858 |
| 9,603,579 B2* | 3/2017 | Lee | A61B 8/0866 |
| 9,891,784 B2* | 2/2018 | Lee | A61B 8/463 |
| 10,043,269 B2 | 8/2018 | Wang et al. | |
| 10,278,674 B2* | 5/2019 | Oh | G06T 15/08 |
| 10,376,241 B2 | 8/2019 | Roundhill | |
| 10,383,599 B2* | 8/2019 | Lee | A61B 8/465 |
| 10,433,815 B2* | 10/2019 | Noguchi | A61B 8/463 |
| 10,702,240 B2* | 7/2020 | Zou | A61B 8/483 |
| 10,772,606 B2* | 9/2020 | Kim | A61B 8/0808 |
| 2009/0156935 A1 | 6/2009 | Frisa et al. | |
| 2011/0282202 A1 | 11/2011 | Lee et al. | |
| 2018/0185003 A1* | 7/2018 | Zou | A61B 8/0808 |
| 2020/0113544 A1* | 4/2020 | Huepf | G06T 7/0012 |
| 2020/0214618 A1* | 7/2020 | Vullings | G16H 50/20 |
| 2020/0234435 A1* | 7/2020 | Raynaud | G06T 3/0093 |
| 2020/0383659 A1* | 12/2020 | Zou | A61B 8/5223 |

FOREIGN PATENT DOCUMENTS

| | | | | |
|---|---|---|---|---|
| CN | 101534717 A | | 9/2009 | |
| CN | 105433981 A | | 3/2016 | |
| CN | 105982685 A | | 10/2016 | |
| CN | 106456112 A | | 2/2017 | |
| CN | 106963378 A | | 7/2017 | |
| EP | 2365356 A2 | | 9/2011 | |
| JP | 2006-167100 A | | 6/2006 | |
| JP | 2015171476 A | * | 10/2015 | |
| WO | WO-2010109514 A1 | * | 9/2010 | A61B 8/08 |
| WO | WO-2016176863 A1 | * | 11/2016 | A61B 8/0808 |
| WO | WO-2018205274 A1 | * | 11/2018 | A61B 8/00 |

OTHER PUBLICATIONS

Kim, Y.B., Kang, S.J., Lee, S.H., Jung, J.Y., Kam, H.R., Lee, J., Kim, Y.S., Lee, J. and Kim, C.H., 2015. Efficiently detecting outlying behavior in video-game players. PeerJ, 3, p. e1502.*
Feng S, Zhou SK, Good S, Comaniciu D. Automatic fetal face detection from ultrasound volumes via learning 3D and 2D information. In2009 IEEE Conference on Computer Vision and Pattern Recognition Jun. 20, 2009 (pp. 2488-2495). IEEE.*
Murphy-Chutorian E, Trivedi MM. Head pose estimation in computer vision: A survey. IEEE transactions on pattern analysis and machine intelligence. Apr. 25, 2008;31(4):607-26.*
Hien LT, Toan DN, Lang TV. Detection of human head direction based on facial normal algorithm. International Journal of Electronics Communication and Computer Engineering. 2015;6(1):110-4.*
Zhu X, Ramanan D. Face detection, pose estimation, and landmark localization in the wild. In2012 IEEE conference on computer vision and pattern recognition Jun. 16, 2012 (pp. 2879-2886). IEEE.*
PCT International Search Report and the Written Opinion dated Feb. 13, 2018, issued in related International Application No. PCT/CN2017/084197, with English machine translation (19 pages).
First Search dated May 30, 2021, issued in related Chinese Application No. 201780079290.5 (4 pages).
First Office Action dated Jun. 3, 2021, issued in related Chinese Application No. 201780079290.5, with English machine translation (20 pages).
PCT International Preliminary Report on Patentability dated Nov. 21, 2019, issued in related International Application No. PCT/CN2017/084197, with English translation (14 pages).

* cited by examiner

ULTRASONIC DEVICE, AND METHOD AND SYSTEM FOR TRANSFORMING DISPLAY OF THREE-DIMENSIONAL ULTRASONIC IMAGE THEREOF

CROSS-REFERENCE TO RELATED PATENT APPLICATION

This application is a U.S. National Stage Application under 35 U.S.C. 371 of International Application No. PCT/CN2017/084197, filed on May 12, 2017, the content of which is incorporated herein by reference in its entirety in the present disclosure.

TECHNICAL FIELD

The present disclosure relates to an ultrasonic device, and in particular to a technique for rotating a three-dimensional ultrasonic image on the ultrasonic device.

BACKGROUND

Prenatal ultrasonic examination is one of the most important examinations that an expectant mother must undergo during the pregnancy, of which the main functions include determining the age of the fetus, analyzing the development of the fetus, detecting fetal malformations or abnormalities, taking photos and dynamic videos of the fetus, and so on. Among them, the fetal face ultrasonic examination can automatically record the facial appearance of the fetus for the expectant mother and detect the facial deformity, and is one of the necessary examinations for the prenatal ultrasonic examination. Because the fetus may be in various positions during the prenatal ultrasonic examination, current fetal face ultrasonic examination requires an experienced doctor to move the probe to find a suitable orientation for imaging according to the position of the fetus, or need the pregnant women to move appropriately to adjust the position of the fetus to facilitate the imaging, which will inevitably increase the cost and time of the examination, and have high demands on the doctor.

SUMMARY

The present disclosure provides ultrasonic devices and three-dimensional ultrasonic image transformation methods and systems which can automatically rotate the ultrasonic three-dimensional volume data of a to-be-examined object to a desired orientation.

According to a first aspect, in one embodiment, a three-dimensional ultrasonic image transformation method is provided, which may include:

obtaining an original ultrasonic three-dimensional volume data including a to-be-examined object;

detecting an orientation of the object from the original ultrasonic three-dimensional volume data according to an image characteristic of the object;

comparing the orientation of the object with a desired orientation to obtain a rotation transformation parameter in a three-dimensional coordinate system;

performing a rotation transformation on the original ultrasonic three-dimensional volume data according to the rotation transformation parameter to obtain a transformed three-dimensional volume data; and outputting the transformed three-dimensional volume data.

According to a second aspect, in one embodiment, a three-dimensional ultrasonic image transformation method is provided, which may include:

obtaining an original ultrasonic three-dimensional volume data including a fetal face;

detecting an orientation of the fetal face from the original ultrasonic three-dimensional volume data according to an image characteristic of the fetal face;

rotating the orientation of the fetal face to obtain a transformed three-dimensional volume data; and, displaying the transformed three-dimensional volume data to obtain an ultrasonic image with a preset view angle.

According to a third aspect, in one embodiment, an ultrasonic device is provided, which may include:

a display;

an ultrasonic probe which is configured to transmit ultrasonic waves to a region of interest in a biological tissue and receive echoes of the ultrasonic waves;

a transmitting/receiving sequence controller which is configured to generate a transmitting sequence and/or a receiving sequence and output the transmitting sequence and/or the receiving sequence to the ultrasonic probe to control the ultrasonic probe to transmit ultrasonic waves to the region of interest and receive echoes of the ultrasonic waves;

a processor which is configured to generate an original ultrasonic three-dimensional volume data including a to-be-examined object according to an ultrasonic echo data, detect an orientation of the object from the original ultrasonic three-dimensional volume data according to an image characteristic of the object, compare the orientation of the object with a desired orientation to obtain a rotation transformation parameter in a three-dimensional coordinate system, perform a rotation transformation one the original ultrasonic three-dimensional volume data according to the rotation transformation parameter to obtain a transformed three-dimensional volume data, and output the transformed three-dimensional volume data to the display to obtain an ultrasonic image.

According to a fourth aspect, in one embodiment, an ultrasonic device is provided, which may include:

a memory which is configured to store programs;

a processor which is configured to implement the methods above by executing the programs stored in the memory.

According to a fifth aspect, in one embodiment, an ultrasonic device is provided, which may include:

a display;

an ultrasonic probe which is configured to transmit ultrasonic waves to a region of interest in a biological tissue and receive echoes of the ultrasonic waves;

a transmitting/receiving sequence controller which is configured to generate a transmitting sequence and/or a receiving sequence and output the transmitting sequence and/or the receiving sequence to the ultrasonic probe to control the ultrasonic probe to transmit ultrasonic waves to the region of interest and receive echoes of the ultrasonic waves;

a processor which is configured to generate an original ultrasonic three-dimensional volume data including an fetal face according to an ultrasonic echo data, detect an orientation of the object from the original ultrasonic three-dimensional volume data according to an image characteristic of the fetal face, rotate the orientation of the fetal face to obtain a transformed three-dimensional volume data, and output the transformed three-dimensional volume data to the display to obtain an ultrasonic image with a preset view angle.

According to a sixth aspect, in one embodiment, an computer-readable storage medium is provided, which may include:

a program which is able to be executed by a processor to implement the methods above.

According to a seventh aspect, in one embodiment, a three-dimensional ultrasonic image transformation system is provided, which may include:

an obtaining unit for obtaining an original ultrasonic three-dimensional volume data including a to-be-examined object;

an orientation detection unit for detecting an orientation of the object from the original ultrasonic three-dimensional volume data according to an image characteristic of the object;

a calculation unit for comparing the orientation of the object with a desired orientation to obtain a rotation transformation parameter in a three-dimensional coordinate system;

a transformation unit for performing a rotation transformation on the original ultrasonic three-dimensional volume data according to the rotation transformation parameter to obtain a transformed three-dimensional volume data; and an image output unit for outputting the transformed three-dimensional volume data to a display to obtain an ultrasonic image.

According to an eighth aspect, in one embodiment, a three-dimensional ultrasonic image transformation system is provided, which may include:

an obtaining unit for obtaining an original ultrasonic three-dimensional volume data including a fetal face;

an orientation detection unit for detecting an orientation of a to-be-examined object from the original ultrasonic three-dimensional volume data according to an image characteristic of the fetal face;

a transformation unit for rotating the orientation of the fetal face to obtain a transformed three-dimensional volume data; and an image output unit for outputting the transformed three-dimensional volume data to a display to obtain an ultrasonic image with a preset view angle.

In the ultrasonic devices and the three-dimensional ultrasonic image transformation methods and systems of the embodiment above, the original ultrasonic three-dimensional volume data including the to-be-examined object may be first obtained, the orientation of the object may be detected from the original ultrasonic three-dimensional volume data according to the image characteristics of the object, and compared with the desired orientation to obtain the rotation transformation parameters in the three-dimensional coordinate system, the rotation transformation may be performed on the original ultrasonic three-dimensional volume data according to the rotation transformation parameters to obtain the transformed three-dimensional volume data, and the transformed three-dimensional volume data may be output. Therefore, the ultrasonic three-dimensional volume data of the measured to-be-examined object can be automatically rotated to the desired orientation without requirement for manual orientation adjustment, and the efficiency can be increased.

DETAILED DESCRIPTION

The present disclosure will be further described in detail below through specific embodiments in combination with the drawings. In different embodiments, similar elements are indicated by similar numbers. In the following embodiments, many details are described so that the present disclosure can be better understood. However, those skilled in the art can effortlessly realize that some of the features can be omitted in different situations, or can be replaced by other elements, materials or methods. In some cases, some operations of the present disclosure are not shown or described in the description, which is to prevent the core part of the present disclosure from being overwhelmed by excessive descriptions. For those skilled in the art, detailed description to theses related operations are not necessary. They can fully understand the related operations according to the description in the description and the general technical knowledge in the field.

In addition, the features, operations, or characteristics described herein can be combined in any suitable manner to form various embodiments. Furthermore, the steps or actions in the method described herein can also be changed or adjusted in the order in a manner obvious to those skilled in the art. Therefore, the various orders in the description and drawings are only for clearly describing a certain embodiment, but not meant to be necessary orders, unless otherwise stated that a certain order must be followed.

The serial numbers for the components herein, such as "first", "second", etc., are only used to distinguish the described objects, but not have any order or technical meaning. The terms "connection" and "coupling" herein include both direct and indirect connections (coupling) unless otherwise stated.

Figure 1:
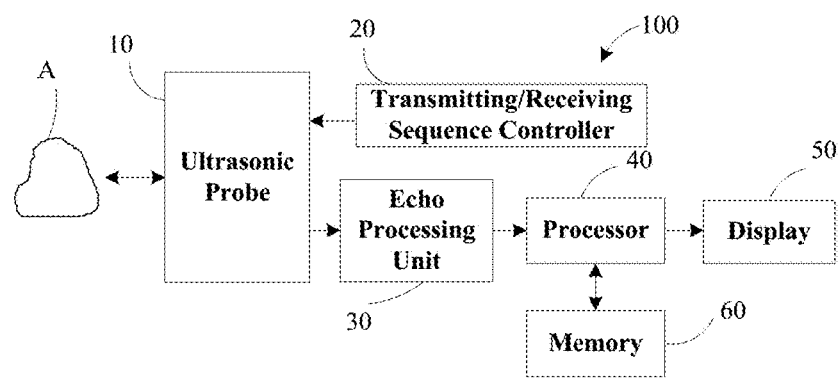
FIG. 1 is a schematic block diagram in one embodiment of the ultrasonic device of the present disclosure.

The present disclosure provides an ultrasonic device. Referring to FIG. 1, the ultrasonic device may include an ultrasonic probe 10, a transmitting/receiving sequence controller 20, an echo processing unit 30, a processor 40, a display 50 and a memory 60. The transmitting/receiving sequence controller 20 may be connected to the ultrasonic probe 10. The ultrasonic probe 10 may be connected to the processor 40 through the echo processing unit 30. The output end of the processor 40 may be connected to the display 50.

The ultrasonic probe 10 may transmit ultrasonic waves to a region of interest A in a biological tissue, and receives echoes of the ultrasonic waves. The ultrasonic probe 10 may include at least one transducer. The transducer may be configured to transmit ultrasonic waves according to the excitation electric signal outputted by the transmission/reception control circuit 120 or convert the received ultrasonic wave into electric signals. Therefore, each transducer may be used to transmit ultrasonic waves to the target of interest in biological tissues, and may also be used to receive ultrasonic echoes returned from the tissues. When performing the ultrasonic examination, it is possible to control which transducers will be used to transmit ultrasonic waves and which transducers will be used to receive ultrasonic waves, or to control the transducers to be used to transmit ultrasonic waves or receive ultrasonic echoes in time-sharing manner, by transmitting and receiving sequences. The transducers participating in the ultrasonic transmission may be excited by the electrical signals simultaneously, thereby transmitting the ultrasonic waves simultaneously. Alternatively, the transducers participating in the ultrasonic transmission may be excited by multiple electrical signals with a certain time interval, thereby continuously transmitting ultrasonic waves with a certain time interval. The ultrasonic probe 10 may be a matrix probe or a volume probe. The volume probe may be an abdominal volume probe or an intracavity volume probe.

The transmitting/receiving sequence controller 20 may be used to control the ultrasonic probe 10 to transmit an ultrasonic beam to the biological tissues on the one hand, and to control the ultrasonic probe 10 to receive ultrasonic echoes of the ultrasonic beam reflected by the tissue on the other hand. In one specific embodiment, the transmitting/receiving sequence controller 20 may be configured to generate a transmitting sequence and/or a receiving sequence, and output the transmitting sequence and/or the receiving sequence to the ultrasonic probe 10 to control the ultrasonic probe 10 to transmit ultrasonic waves to the region of interest A and receive the echoes of the ultrasonic waves. The transmission sequence may be used to control a part or all of the multiple transducers to transmit ultrasonic waves to the target of interest in the biological tissue. The parameters of the transmitting sequence may include the number of the transducers used in the transmitting and the ultrasound transmitting parameters (such as amplitude, frequency, number of transmitting, transmitting interval, transmitting angle, wave pattern, etc.). The receiving sequence may be used to control a part or all of the multiple transducers to receive the ultrasound echoes reflected by the tissue. The parameters of the receiving sequence may include the number of the transducers used in the receiving and the receiving parameters of the echo (such as the receiving angle, depth, etc.). Depending on the application of the ultrasound echo or the images generated based on the ultrasound echo, the ultrasound parameters in the transmitting sequence and the echo parameters in the receiving sequence may also be different.

The echo processing unit 30 may be configured to process an ultrasonic echoes, for example, to perform processing such as filtering, amplification, and beam-forming, etc. on an ultrasonic echo signals. The ultrasonic echoes received by the ultrasonic probe 10 may be processed by the echo processing unit 30 and outputted to the processor 40. Those skilled in the art should understand that, in some embodiments, the echo processing unit 30 may be omitted when it is not necessary to perform processing such as filtering, amplifying, and beam-forming, etc. on the ultrasonic echoes.

The memory 60 may be used to store programs and data, such as ultrasonic echo data or image data.

The processor 40 may be configured to execute a program or process data. In the present embodiment, the processor may be configured to perform a transformation of a three-dimensional ultrasonic image. Specifically, the processor 40 may generate an original ultrasonic three-dimensional volume data including the to-be-examined object according to the ultrasonic echo data, detect the orientation of the object from the original three-dimensional volume data according to the image characteristics of the object, compare the detected orientation of the object with the desired orientation to obtain the rotation transformation parameters in the three-dimensional coordinate system, perform the rotation transformation one the original three-dimensional volume data to obtain transformed three-dimensional volume data, and output the transformed three-dimensional volume data to the display for display to obtain an ultrasonic image. The rotation transformation may be implemented by a rotation axis and a rotation angle. Correspondingly, the rotation transformation parameters may include a position of the rotation axis and a rotation angle (such as an Euler angle). There may be multiple rotation axes and rotation angles. Of course, the rotation transformation may also be implemented by a rotation matrix, and accordingly, the rotation transformation parameters may include the rotation matrix.

The image characteristics may include image characteristics corresponding to the anatomical structure of one or more tissues of the to-be-examined object d in the ultrasonic three-dimensional volume data. The image characteristics may include the color characteristics, texture characteristics, shape characteristics, spatial relationship characteristics or the like.

Figure 2:
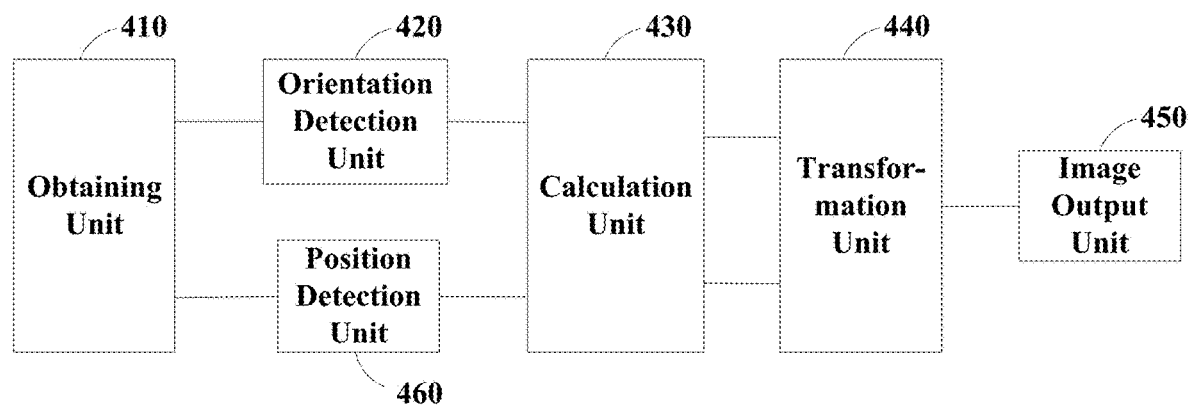
FIG. 2 is a schematic block diagram in one embodiment of the transformation system of the three-dimensional ultrasonic image of the present disclosure.

In one embodiment, referring to FIG. 2, a system for implementing the transformation of the three-dimensional ultrasonic image in the ultrasonic device may include an obtaining unit 410, an orientation detection unit 420, a calculation unit 430, a transformation unit 440 and an image output unit 450. The functions of the system may be implemented in whole or in part by the processor 40.

The obtaining unit 410 may be configured to obtain the original ultrasonic three-dimensional volume data including the to-be-examined object.

The orientation detection unit 420 may be configured to detect the orientation of the object from the original ultrasonic three-dimensional volume data according to the image characteristics of the object.

The calculation unit 430 may be configured to compare the orientation of the object with the desired orientation to obtain the rotation transformation parameters in the three-dimensional coordinate system.

The transformation unit 440 may be configured to perform the rotation transformation on the original ultrasonic three-dimensional volume data according to the rotation transformation parameters to obtain transformed three-dimensional volume data.

The image output unit 450 may be configured to output the transformed three-dimensional volume data to the display to obtain an ultrasonic image, that is, an ultrasonic image corresponding to the three-dimensional volume data which can be observed from the display.

Figure 3:
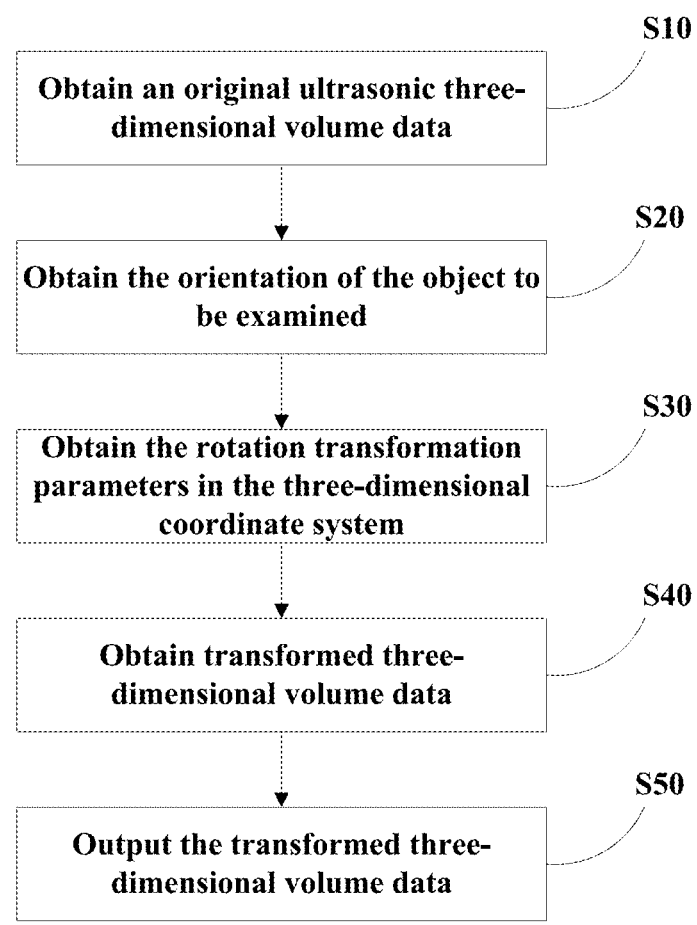
FIG. 3 is a flow chart of a method for transforming the three-dimensional ultrasonic image of the present disclosure.

Based on the ultrasonic device above, the specific processing process for transforming the three-dimensional ultrasonic image may be shown in FIG. 3, which may include the following steps.

In step S10, the obtaining unit 410 may obtain the original ultrasonic three-dimensional volume data including the to-be-examined object, i.e., generate the original ultrasonic three-dimensional volume data including the to-be-examined object according to the ultrasonic echo data. Specifically, the obtaining unit 410 may generate multiple two-dimensional images according to the ultrasonic echo data obtained by scanning multiple scanning planes with the ultrasonic probe 10, perform coordinate transformation on the multiple two-dimensional images according to the spatial positions of the multiple scanning planes of the ultrasonic probe 10, and perform interpolation thereon to generate the original ultrasonic three-dimensional volume data of the object. The obtaining unit 410 may further perform image optimization processing on the generated original ultrasonic three-dimensional volume data, such as smoothing, denoising, etc., so as to facilitate subsequent processing.

In step S20, the orientation detection unit 420 may detect the orientation of the to-be-examined object from the original ultrasonic three-dimensional volume data according to the image characteristics of the object.

In step S30, the calculation unit 430 may compare the detected orientation of the object with the desired orientation to obtain the rotation transformation parameters in the three-dimensional coordinate system.

In step S40, the transformation unit 440 may perform the rotation transformation on the original ultrasonic three-dimensional volume data according to the rotation transformation parameters to obtain the transformed three-dimensional volume data. The transformation unit 440 may also perform clipping, image editing, volume data segmentation or other processing on the three-dimensional volume data. The clipping may include VOI clipping, plane clipping, geometry clipping, erasing (eraser), and the like.

Figure 4:
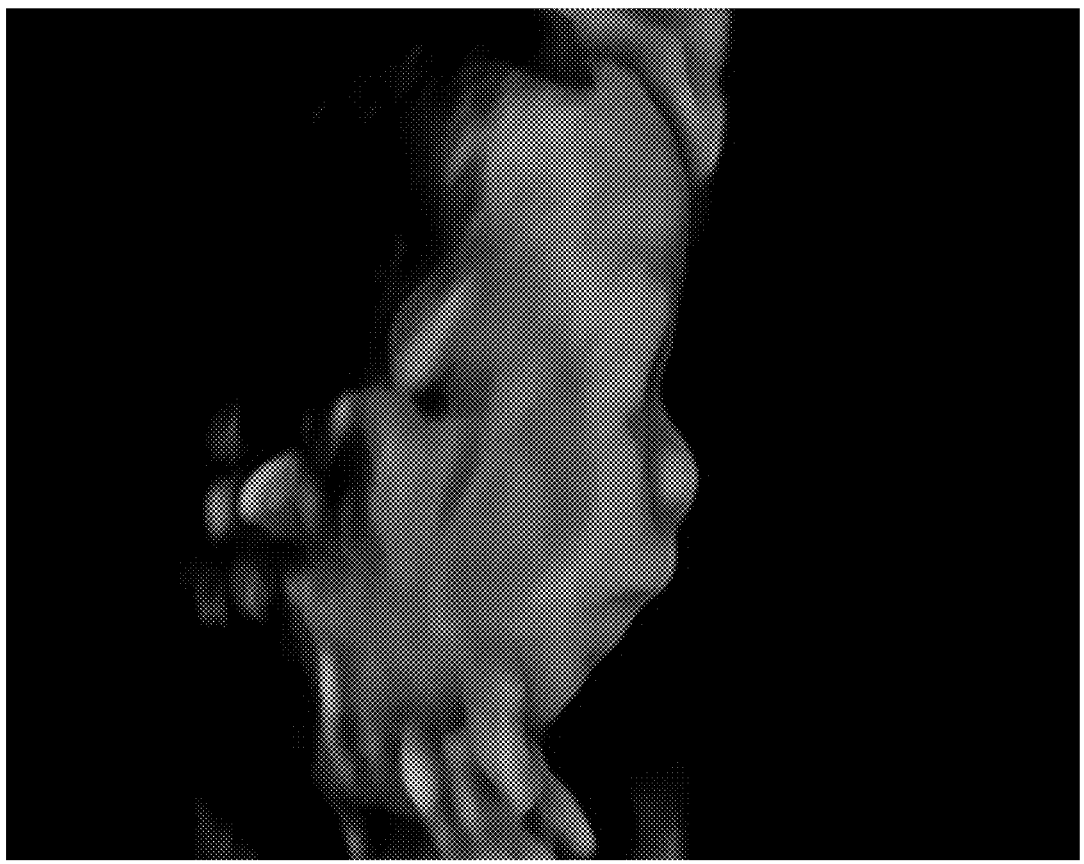
FIG. 4 is an image of the original ultrasonic three-dimensional volume data displayed on the display in one embodiment of the ultrasonic device of the present disclosure.
Figure 5:
FIG. 5 is an image of the rotating-transformed three-dimensional volume data displayed on the display in one embodiment of the ultrasonic device of the present disclosure.

In step S50, the image output unit 450 may output the transformed three-dimensional volume data to the display 50 to obtain an ultrasonic image. Taking the object being the fetal face as an example, and referring to FIG. 4 and FIG. 5, the original ultrasonic three-dimensional volume data which is not rotated and shown on the display 50 is as shown in FIG. 4, in which the fetal face is not facing the user and the left face is completely occluded. By using the ultrasonic device of the present embodiment, the three-dimensional volume data may be automatically rotated to obtain the face image shown in FIG. 5, such that the user can observe the face of the fetus. In FIG. 5, the face of the fetus is toward the lateral side in 45 degree, and most facial features are visible. The outline is clear, and the center contour line can be well displayed. Therefore, the ultrasonic three-dimensional volume data of the to-be-examined object can be automatically rotated to a desired orientation without manual adjustment by a doctor, which improves the efficiency of the ultrasonic examination.

The desired orientation may be set by the user in advance. Alternatively, the default setting of the desired orientation may be adopted. Alternatively, the desired orientation may be the optimal orientation determined based on the current original three-dimensional volume data. The desired orientation may specifically include a preset viewing angle. The optimal orientation may be determined according to the current original three-dimensional volume data. For example, the optimal orientation may be an orientation where the object may be completely displayed in the display window on the screen of the display 50. Specifically, the desired orientation may be an orientation where the ultrasonic image of the object may be displayed in the display window facing the user (frontal orientation), that is, a front view angle. Alternatively, the desired orientation may be an orientation where the three-dimensional volume data of the object may be displayed in the display window with its side facing the user (side orientation), that is, left or right side angle. Alternatively, the desired orientation may be an orientation where the ultrasonic image of the object may be displayed in the display window with its top facing the user (top orientation), that is, the top view angle. Of course, there may be multiple desired orientations. For example, three desired orientations may be set, including a front orientation, a side orientation and a top orientation. When there are multiple desired orientations, the ultrasonic images in the respective orientations may be sequentially displayed according to a user selection or a preset order.

Further, the three-dimensional ultrasonic image transformation system may include a position detection unit 460. The position detecting unit 460 may detect the position of the object from the original ultrasonic three-dimensional volume data according to the image characteristics of the object before or after the transformation unit 440 obtains the transformed three-dimensional volume data. The calculation unit 430 may determine the relative position of the object in the display window according to the position of the object, and compare the relative position of the object with the desired position of the object in the display window to obtain the displacement vector or coordinate differences in the three-dimensional coordinate system. Further, the transformation unit 440 may move the three-dimensional volume data according to the displacement vector or the coordinate differences, such that the object is moved to the desired position in the display window. The user only needs to set the desired position of the object in the display window to achieve the position adjustment and movement of the three-dimensional ultrasonic image. In connection with the automatic rotation described above, various transformation of the three-dimensional ultrasonic image may be achieved, thereby meeting the requirements of different ultrasonic examinations of the user. Similarly, the desired position may be set in advance, or may be an optimal position determined according to the current original three-dimensional volume data. For example, the desired position may be the position where the object is in the center of the display window. In the present embodiment, the position of the object may be the position coordinates of the object in the three-dimensional coordinate system. In the case that the three-dimensional coordinate system is a three-dimensional coordinate system with the display window being the reference object, the process of "determining the relative position of the object in the display window according to the position of the object" may be omitted, thereby saving the processing flow.

The method for the orientation detection unit 420 to detect the orientation of the to-be-examined object from the original ultrasonic three-dimensional volume data according to the image characteristics of the object and the method for the position detection unit 460 to detect the position of the object from the original ultrasonic three-dimensional volume data according to the image characteristics of the object may be the same or different. For example, in the first embodiment, the orientation detection unit 420 may detect the orientation of the object from the original ultrasonic three-dimensional volume data according to the image characteristics of the object. Specifically, the orientation detection unit 420 may input the original ultrasonic three-dimensional volume data to a machine learning model which has been obtained by training using the samples in which the correspondence between the image characteristics and the orientation of the object had been known to obtain the orientation of the object. The training of the machine learning model may be performed by one or more of deep learning, support vector machine, random forest, and adaboost.

Similarly, the position detection unit 460 may also use the methods above to detect the position of the object. Specifically, the position detection unit 460 may input the original ultrasonic three-dimensional volume data to a machine learning model which has been obtained by training using the samples in which the correspondence between the image characteristics and the position of the object had been known to obtain the position of the object.

In a second embodiment, the orientation detection unit 420 may detect the orientation of the to-be-examined object from the original ultrasonic three-dimensional volume data according to the image characteristics of the object. Specifically, the orientation detection unit 420 may automatically detect one or more anatomical structures from the original ultrasonic three-dimensional volume data according to the image characteristics of the to-be-examined object and obtain the orientation of the object according to the detected anatomical structures. The image processing algorithms may be used to automatically detect the one or more anatomical structures. The image processing algorithms may include one or more of template matching algorithms, edge extraction algorithms, image transformation algorithms, morphological operation algorithms and image segmentation algorithms. For example, the image segmentation algorithm may be used to detect the one or more anatomical structures. The image segmentation algorithms may include one or more of a graphcut algorithm, an active contour model algorithm and an active shape model algorithm. It may also be possible to build a mathematical model of the to-be-examined object from the original ultrasonic three-dimensional volume data according to the image characteristics of the object using the image processing algorithm and analyzing the original ultrasonic three-dimensional volume data using the mathematical model to obtain the one or more anatomical structures of the object.

Similarly, the position detection unit 460 may automatically detect one or more anatomical structures from the original ultrasonic three-dimensional volume data according to the image characteristics of the to-be-examined object, and obtain the position of the object according to the detected anatomical structures.

In a third embodiment, the ultrasonic device may further include a human-computer interaction device, such as a trackball, a mouse, a keyboard, a touch screen, or the like. The orientation detection unit 420 may detect the orientation of the object from the original ultrasonic three-dimensional volume data according to the image characteristics of the object specifically by the orientation detection unit 420 outputting the original ultrasonic three-dimensional volume data to the display for display to obtain an ultrasonic image, detecting one or more marker points inputted by the user on the ultrasonic image through the human-computer interaction device, and obtaining the orientation of the object according to the marker points. The one or more marker points may correspond to one or more anatomical structures of the object on the ultrasonic image. That is, in the third embodiment, the detection of the one or more anatomical structures of the to-be-examined object may be completed by the user through the human-computer interaction device, which is a semi-automatic detection mode (in the first embodiment and the second embodiment, it is fully automatic detection).

Similarly, the position detection unit 460 may output the original ultrasonic three-dimensional volume data to the display for display to obtain an ultrasonic image, detect one or more marker points inputted by the user on the ultrasonic image, and obtain the position of the object according to the marker points.

In a fourth embodiment, the three-dimensional ultrasonic image transformation system may also use both or all methods for obtaining the orientation or position of the object in the two or three embodiments above. That is, the transformation system in the fourth embodiment may use corresponding method to obtain the orientation or position of the object according to the user's selection. Using multiple methods to determine the orientation or position of the object can improve the accuracy.

Figure 6:
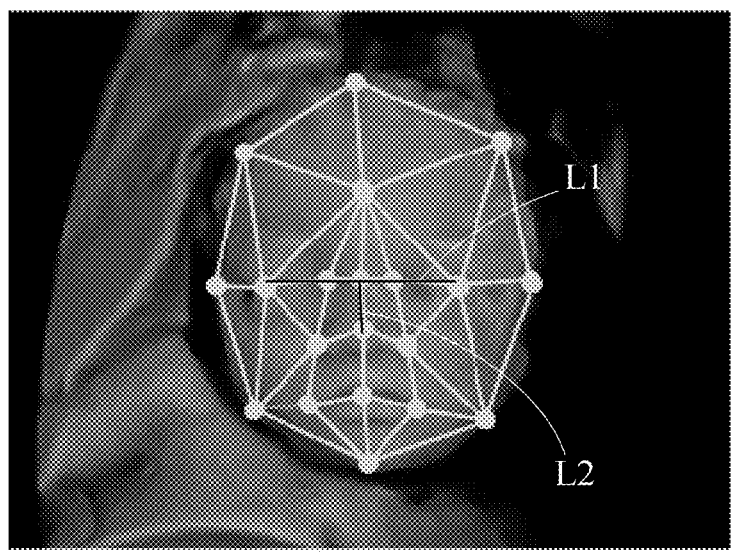
FIG. 6 is a first schematic diagram of the first connection line and the second connection line in one embodiment of the ultrasonic device of the present disclosure.
Figure 7:
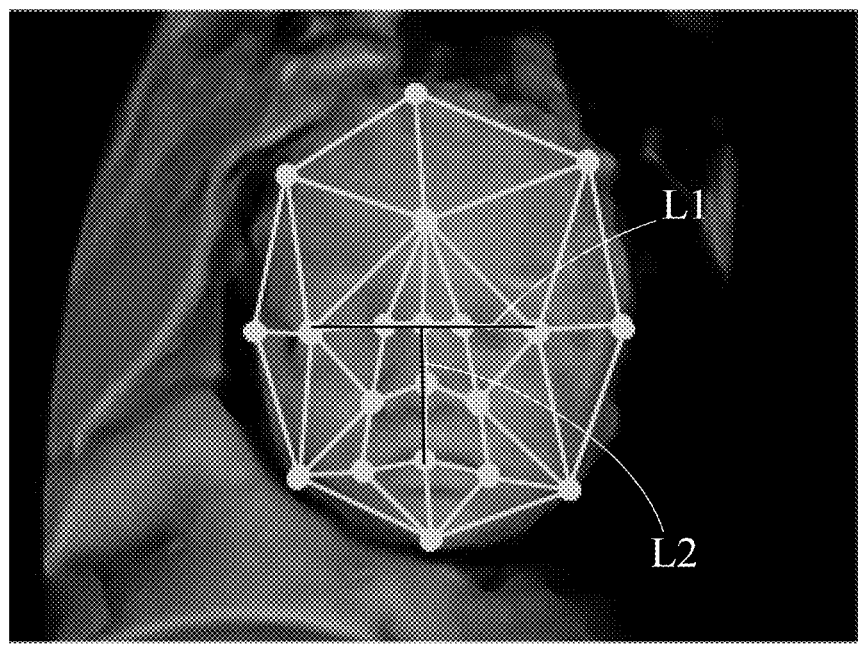
FIG. 7 is a second schematic diagram of the first connection line and the second connection line in one embodiment of the ultrasonic device of the present disclosure.

Referring to FIG. 6 and FIG. 7, the region of interest A may be various organs, and the object may be a part to-be-examined organ. In the present embodiment, the region of interest A is a uterus, and the object is a fetal face. Correspondingly, the image characteristics of the fetal face may include the image characteristics corresponding to at least two anatomical structures located on the fetal face. The at least two anatomical structures may be selected from fetal eyes, fetal nose, fetal mouth, fetal forehead, fetal chin, fetal cheek, fetal face contour and fetal ear. The transformation system may identify the orientation of the fetal face in the three-dimensional volume data according to the position of the image characteristics of the fetal face, and may also identify the relative position of the fetal face in the display window (that is, the coordinates of the fetal face in the three-dimensional coordinate system).

The orientation may include the facing direction of the front and top of the object. In the present embodiment, the orientation may include the facing direction of the fetal face and the top of the fetal head.

Taking the to-be-examined object being a fetal face as an example, the specific process of transforming the three-dimensional ultrasonic image may include the following steps.

In S10, the obtaining unit 410 may obtain an original ultrasonic three-dimensional volume data including a fetal face.

In step S20, the orientation detection unit 420 may detect the orientation of the fetal face from the original ultrasonic three-dimensional volume data according to the image characteristics of the fetal face.

In step S40, the transformation unit 440 may adjust the orientation of the fetal face by rotation to obtain transformed three-dimensional volume data.

In step S50, the image output unit 450 may output the transformed three-dimensional volume data to the display 50. The display 50 may display the transformed three-dimensional volume data, thereby obtaining an ultrasonic image with a preset view angle.

Before step S40, the method may further include a step in which the image output unit 450 may output the original ultrasonic three-dimensional volume data to the display 50 and the display 50 may display the original ultrasonic three-dimensional volume data to obtain a first ultrasonic image. That is, the user can observe the first ultrasonic image representing the original ultrasonic three-dimensional volume data through the display 50.

Specifically, in step S40, the transformation unit 440 may receive, via the human-machine interaction device, a first rotation instruction generated when the user inputs one or more markers on the first ultrasonic image, and rotate the fetal face around a rotation axis built based on the one or more markers according to the first rotation instruction to obtain the three-dimensional volume data corresponding to the fetal face at a preset view angle as the transformed three-dimensional volume data.

Specifically, in step S50, the image output unit 450 may output the three-dimensional volume data corresponding to the fetal face at the preset view angle to the display 50. The display 50 may display the three-dimensional volume data, thereby obtaining an ultrasonic image at the preset view angle. The preset view angle may include at least one of a front of the fetal face, a side of the fetal face, and a 45-degree angle oblique front of the fetal face.

The one or more marker points may correspond to one or more of the fetal eye, the fetal nose, the fetal mouth, the fetal forehead, the fetal chin, the fetal cheek and the fetal ear on the first ultrasonic image.

The rotation instruction may be automatically generated based on the marker points. Of course, the rotation instructions may also be inputted directly by the user. For example, before step S40, the transformation unit 440 may receive a second rotation instruction obtained by the user's input through the human-machine interaction device. Correspondingly, in step S40, the transformation unit 440 may rotate the fetal face according to the second rotation instruction to obtain the transformed three-dimensional volume data.

The second rotation instruction may correspond to one or more preset view angles. For example, the second rotation instruction may correspond to the front of the fetal face, the 45-degree oblique front angle of the fetal face, and the side of the fetal face. Three corresponding buttons may be arranged on the human-machine interactive device, such as buttons marked with 0°, 45° and 90°. The user may press the 0° button. Since the 0° button corresponds to the 45-degree oblique front angle of the fetal face, the transformation unit 440 may rotate the orientation of the fetal face such that the user can observe the ultrasonic image of the fetal face at the 45-degree oblique front angle on the display 50. The operations of the 45° button and the 90° button are similar. Of course, it is also possible to arrange only one button, and cycle through the three preset angles by the number of times the button is pressed.

Referring to FIG. 6, the orientation detection unit 420 may obtain the orientation of the fetal face according to the detected anatomical structures or according to the marker points by the following steps.

The orientation detection unit 420 may obtain a first connection line L1 according to the detected fetal eyes. The eyes may include the canthuses of both eyes. For example, in one embodiment, the orientation detection unit 420 may connect the canthuses of the two eyes with a line, and such line may be the first connection line L1. The fetal eyes may be automatically detected from the original ultrasonic three-dimensional volume data. Alternatively, the fetal eyes may be obtained according to the marker points related to the fetal eyes inputted by the user on the ultrasonic image.

Figure 8:
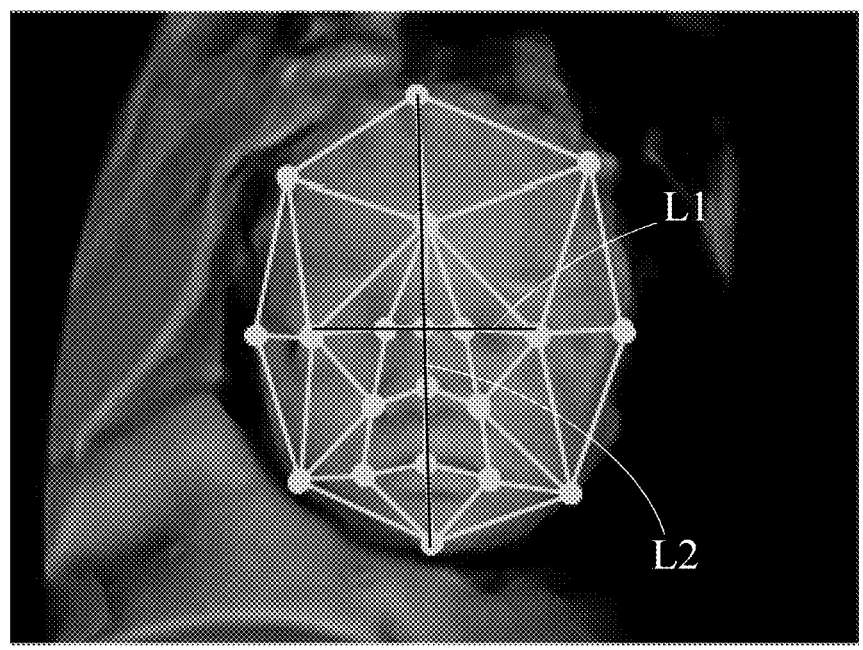
FIG. 8 is a third schematic diagram of the first connection line and the second connection line in one embodiment of the ultrasonic device of the present disclosure.

The orientation detection unit 420 may obtain a second connection line L2 according to any two of the midpoint of the first connection line L1, the fetal nose and the fetal mouth. For example, in one embodiment, the fetal nose may be represented by the nose tip. The second connection line L2 may be a line connecting the midpoint of the first line L1 and the nose tip of the fetus, or a line obtained by fitting with the midpoint of the first line L1 and the nose tip of the fetus, as shown in FIG. 6. The fetal mouth may be represented by the corner of the mouth and/or the midpoint of the mouth. In another embodiment, the second connection line L2 may be a line connecting the midpoint of the first connection line L1 and the midpoint of the fetal mouth, as shown in FIG. 7. Similarly, the second line L2 may be obtained in other way, which will not be repeatedly described here. Alternatively, the second line L2 may also be a line connecting, or a line obtained by fitting with, multiple points on the fetal face contour line in the center of the fetal face in the original ultrasonic three-dimensional volume data, as shown in FIG. 8.

The orientation detection unit 420 may obtain the orientation of the fetal face according to the first connection line L1 and the second connection line L2. Specifically, the orientation of the fetal face may include at least two of the left-right direction of the face, the up-down direction of the face (the facing direction of the fetal head) and the front-back direction of the face (the facing direction of the fetal face). In the present embodiment, the orientation may include the three directions above. The orientation detection unit 420 may obtain the normal of a plane determined by the first connection line L1 and the second connection line L2, and determine the direction in which the normal extends toward the outside of the three-dimensional volume data to be the facing direction of the fetal face. Alternatively, the orientation detection unit 420 may determine the facing direction of the fetal face (that is, the front-to-back direction of the fetal face) according to the plane and the fact that the nose tip is the high point of the face. The orientation detection unit 420 may determine the left-right direction of the face according to the facing direction of the fetal face and the two extending directions of the first connection line L1. Similarly, the orientation detection unit 420 may determine the up-down direction of the face according to the left-right direction of the fetal face and the two extending directions of the second connection line L2.

Regardless of which anatomical structure is initially detected, its position relationship with other anatomical structures may be identified according to the marker points of such anatomical structure or by an automatic detection, thereby detecting the orientation of the object in the original ultrasonic three-dimensional volume data. For example, the first connection line in the embodiment above is obtained based on the detection of the fetal eyes. Alternatively, any one of the fetal nose, the fetal forehead, the fetal chin, the fetal cheek, the fetal ear, the contour of fetal face and the fetal mouth may be used to replace the fetal eyes to obtain the first connection line, and obtain the second connection line according to the remaining anatomical structure, so as to determine the orientation of the fetal face. In one embodiment, the connection lines connecting the positions of at least two of the fetal eyes, the fetal nose, the fetal mouth, the fetal forehead, the fetal chin, the fetal cheek, the fetal face contour and fetal ear, etc. in ultrasonic three-dimensional volume data may be used to detect the orientation of the fetal face in the original ultrasonic three-dimensional volume data.

The ultrasonic image above may include a rendering image representing the face of the fetus. The image output unit 450 may render the original ultrasonic three-dimensional volume data or the transformed three-dimensional volume data, obtain the rendering image according to the transformed three-dimensional volume data, and output the rendering image to the display 50 for display. Accordingly, the user can observe the rendering image representing the facial features of the fetus on the display 50.

Further, the ultrasonic image above may include a clinical section image of the fetal face. The image output unit 450 may obtain the clinical section of the fetal face in the original three-dimensional volume data and obtain the image data of the clinical section of the fetal face, and output the image data to the display 50 for display, thereby obtaining the clinical section image of the fetal face. The clinical section of the fetal face may be one or more of the horizontal orbital cross section, the median sagittal section, the forehead coronal section and the nasolabial coronal section. The section image may be a cross section image, a sagittal section image, a coronal section image, or a section image at any other angle. The image output unit 450 may also perform rendering on the section image to obtain a corresponding rendered image.

Further, the three-dimensional ultrasonic image transformation system may include a setting unit (not shown in the figure). The setting unit may set the working modes and parameters of other units in the system. Specifically, the setting unit may provide a selection function of selecting whether to enable the transformation unit 440 to perform rotation transformation and movement on the original ultrasonic three-dimensional volume data, and, in the case that it is enabled, provide a selection function of selecting whether to enable the image output unit 450 to obtain the transformed three-dimensional volume data. After receiving the selection instruction of the user, the setting unit may perform corresponding enable or disable operation. The setting unit may also provide a selection function of selecting whether to enable the orientation detection unit 420 and/or the position detection unit 460 to detect the orientation and/or the position of the to-be-examined object before rotating and/or moving the three-dimensional volume data. In the case that there is the detection step, the setting unit may select the detection modes, such as the detection targets (anatomical structures, markers, face positions, face orientation, etc.), the detection methods (image processing methods, image segmentation methods, machine learning methods, whether to build face models, etc.), fully automatic detection or semi-automatic detection, the kinds of information which needs to be inputted by the user in semi-automatic detection, etc.

The ultrasonic device may further include an adjustment unit (not shown in the figure), which may provide the user with a function of manually adjusting the rendering image and the clinical section image of the fetal face. Specifically, the adjustment unit may be configured to adjust the preset view angle (the view angle of the rendering image) according to an instruction inputted by the user. For example, it may be adjusted from the current view angle to the view angle of the front of the fetal face, the side of the fetal face, the top/bottom view of the fetal face, a view angle formed by deflecting the view angle above by a certain angle, or the combination thereof. The adjustment unit may also adjust the clinical section image of the fetal face according to the instruction inputted by the user. For example, the adjustment unit may adjust the angle and/or position of the section image by rotating and/or moving the three-dimensional volume data so as to obtain a better section image.

Those skilled in the art may understand that all or a part of the functions of the various methods in the embodiments above may be implemented by the hardware (such as the processor) or by computer programs. When all or a part of the functions in the embodiments above are implemented by the computer program, the program may be stored in a computer-readable storage medium. The storage medium may include a read-only memory, a random access memory, a magnetic disk, an optical disk or a hard disk, etc. The computer may execute the program to implement the functions above. For example, the program may be stored in the memory of the device, and when the processor executes the program in the memory, all or a part of the functions described above may be implemented. In addition, when all or a part of the functions in the embodiments above are implemented by the computer program, the program may also be stored in a storage medium such as a server, another computer, a magnetic disk, an optical disk, a flash disk, or a mobile hard disk, etc., and may be downloaded or saved to the memory of the local device, or be used to update the system of the local device. When the program in the memory is executed by the processor, all or a part of the functions in the embodiments above may be implemented.

Specific examples have been used to illustrate the present disclosure above. However, they are only used to facilitate the understanding to, but not intended to limit, the present disclosure. For those skilled in the art, several simple deductions, modification or replacements may be made according to the concepts of the present disclosure.

The invention claimed is:

1. A three-dimensional ultrasonic image transformation method, comprising:
   obtaining an original ultrasonic three-dimensional volume data containing an object to be examined;
   detecting an orientation of the object with respect to the original ultrasonic three-dimensional volume data according to an image characteristic of the object, wherein the detecting comprises:
   identifying one or more anatomical structures in the object;
   obtaining a first connection line according to the identified one or more anatomical structures;
   obtaining a second connection line according to the identified one or more anatomical structures, the second connection line connecting a midpoint of the first connection line to one of the one or more anatomical structures;
   obtaining a normal of a plane that is determined by the first connection line and the second connection line; and
   obtaining the orientation of the object according to the normal of the plane;
   determining an optimal orientation for the object based on the original ultrasonic three-dimensional volume data;
   comparing the orientation of the object with the optimal orientation to obtain a rotation transformation parameter in a three-dimensional coordinate system;
   performing a rotation transformation on the original ultrasonic three-dimensional volume data according to the rotation transformation parameter to obtain a transformed three-dimensional volume data, wherein when the object is a fetal face, the rotation transformation on the original ultrasonic three-dimensional volume data automatically rotates the fetal face such that a user can observe the fetal face;
   detecting a position of the object from the original ultrasonic three-dimensional volume data according to the image characteristic of the object;
   determining a relative position of the object in a display window according to the position of the object;
   comparing the relative position of the object with a desired position of the object in the display window to obtain a displacement vector or a coordinate difference in the three-dimensional coordinate system; and
   performing a coordinate transformation of the transformed three-dimensional volume data according to the displacement vector or the coordinate difference to translate the object to the desired position in the display window; and outputting the transformed three-dimensional volume data after the rotation transformation and the coordinate transformation.

2. The method of claim 1, wherein the image characteristic comprises an image characteristic corresponding to the one or more anatomical structures in the object in the original ultrasonic three-dimensional volume data.

3. The method of claim 1, wherein the orientation of the object with respect to the original ultrasonic three-dimensional volume data is detected according to the image characteristic of the object by one of:
inputting the original ultrasonic three-dimensional volume data into a machine learning model to obtain the orientation of the object with respect to the original ultrasonic three-dimensional volume data, wherein the machine learning model has been obtained by training using samples in which correspondences between image characteristics and orientations of the object are known;
outputting the original ultrasonic three-dimensional volume data to a display to obtain an ultrasonic image, detecting one or more marker points inputted by an user on the ultrasonic image, and obtaining the orientation of the object with respect to the original ultrasonic three-dimensional volume data according to the one or more marker points, wherein the one or more marker points correspond to the one or more anatomical structures of the object in the ultrasonic image; or
automatically identifying the one or more anatomical structures from the original ultrasonic three-dimensional volume data according to the image characteristic of the object, and obtaining the orientation of the object with respect to the original ultrasonic three-dimensional volume data according to the identified one or more anatomical structures.

4. The method of claim 1, wherein the one or more anatomical structures are selected from a fetal eye, a fetal nose, a fetal forehead, a fetal chin, a fetal cheek, a fetal ear, a fetal face contour and a fetal mouth.

5. The method of claim 4, wherein the orientation of the object is obtained according to the identified one or more anatomical structures or according to the marker points by:
obtaining the first connection line according to identified fetal eyes;
obtaining the second connection line according to any two of a midpoint of the first connection line, the fetal nose and the fetal mouth; and
obtaining the orientation of the fetal face according to the first connection line and the second connection line.

6. The method of claim 1, wherein the orientation comprises a direction of the fetal face and a direction of a top of a fetal head.

7. The method of claim 1, wherein outputting the transformed three-dimensional volume data comprises: rendering the transformed three-dimensional volume data to obtain a rendering image representing the fetal face, and outputting the rendering image.

8. The method of claim 7, wherein outputting the transformed three-dimensional volume data further comprises: obtaining an image of a clinical specific section of the fetal face according to the transformed three-dimensional volume data, and outputting the image of the clinical specific section of the fetal face.

9. A three-dimensional ultrasonic image transformation method, comprising:
obtaining an original ultrasonic three-dimensional volume data containing a fetal face;
detecting an orientation of the fetal face with respect to the original ultrasonic three-dimensional volume data according to an image characteristic of the fetal face, wherein the detecting comprises:
identifying at least two anatomical structures in the fetal face;
obtaining a first connection line according to the identified at least two anatomical structures;
obtaining a second connection line according to the identified at least two anatomical structures, the second connection line connecting a midpoint of the first connection line to one of the at least two anatomical structures;
obtaining a normal of a plane that is determined by the first connection line and the second connection line; and
obtaining the orientation of the fetal face according to the normal of the plane;
determining an optimal orientation for the original ultrasonic three-dimensional volume data containing the fetal face such that a user can observe the fetal face;
rotating the orientation of the fetal face according to the optimal orientation to obtain a transformed three-dimensional volume data;
detecting a position of the fetal face from the original ultrasonic three-dimensional volume data according to the image characteristic of the fetal face;
determining a relative position of the fetal face in a display window according to the position of the fetal face;
comparing the relative position of the fetal face with a desired position of the fetal face in the display window to obtain a displacement vector or a coordinate difference in the three-dimensional coordinate system; and
performing a coordinate transformation of the transformed three-dimensional volume data according to the displacement vector or the coordinate difference to translate the fetal face to the desired position in the display window; and
displaying the transformed and translated three-dimensional volume data.

10. The method of claim 9, wherein the image characteristic comprises image characteristics corresponding to the at least two anatomical structures on the fetal face.

11. The method of claim 9, wherein the at least two anatomical structures are selected from a fetal eye, a fetal nose, a fetal mouth, a fetal forehead, a fetal chin, a fetal cheek, a fetal face contour and a fetal ear.

12. The method of claim 9, before rotating the orientation of the fetal face according to the optimal orientation to obtain the transformed three-dimensional volume data, further comprising:
displaying the original ultrasonic three-dimensional volume data to obtain a first ultrasonic image, and receiving a first rotation instruction generated by a user inputting one or more marker points on the first ultrasonic image;
wherein rotating the orientation of the fetal face according to the optimal orientation to obtain the transformed three-dimensional volume data comprises:
rotating the orientation of the fetal face around a rotation axis built with the one or more marker points according to the first rotation instruction to form the transformed three-dimensional volume data in which the fetal face is at a preset view angle.

13. The method of claim 12, wherein the preset view angle comprises at least one of a front of the fetal face, a side of the fetal face and a 45-degree angle oblique front of the fetal face.

14. The method of claim 12, wherein the one or more marker points correspond to one or more of a fetal eye, a fetal nose, a fetal mouth, a fetal forehead, a fetal chin, a fetal cheek and a fetal ear in the first ultrasonic image.

15. The method of claim 9, before rotating the orientation of the fetal face according to the optimal orientation to obtain the transformed three-dimensional volume data, further comprising:
receiving a second rotation instruction generated by a user inputting one time;
wherein rotating the orientation of the fetal face according to the optimal orientation to obtain the transformed three-dimensional volume data comprises:
rotating the orientation of the fetal face according to the second rotation instruction to obtain the transformed three-dimensional volume data.

16. The method of claim 9, wherein the orientation of the fetal face with respect to the original ultrasonic three-dimensional volume data is detected according to the image characteristic of the fetal face by one of:
inputting the original ultrasonic three-dimensional volume data into a machine learning model to obtain the orientation of the fetal face with respect to the original ultrasonic three-dimensional volume data, wherein the machine learning model has been obtained by training using samples in which correspondences between image characteristics and orientations of the fetal face are known;
outputting the original ultrasonic three-dimensional volume data to a display to obtain an ultrasonic image, detecting one or more marker points inputted by an user on the ultrasonic image, and obtaining the orientation of the fetal face with respect to the original ultrasonic three-dimensional volume data according to the one or more marker points, wherein the one or more marker points correspond to one or more of a fetal eye, a fetal nose, a fetal mouth, a fetal forehead, a fetal chin, a fetal cheek and a fetal ear in the ultrasonic image; or
automatically identifying the at least two anatomical structures from the original ultrasonic three-dimensional volume data according to the image characteristic of the fetal face, and obtaining the orientation of the fetal face with respect to the original ultrasonic three-dimensional volume data according to the at least two anatomical structures identified automatically.

17. A non-transitory computer-readable storage medium, comprising a program, wherein the program is able to be executed by a processor to cause the processor to:
obtain an original ultrasonic three-dimensional volume data containing an object to be examined according to an ultrasonic echo data;
detect an orientation of the object with respect to the original ultrasonic three-dimensional volume data according to an image characteristic of the object, wherein the detection of the orientation of the object comprises:
identifying one or more anatomical structures in the object;
obtaining a first connection line according to the identified one or more anatomical structures;
obtaining a second connection line according to the identified one or more anatomical structures, the second connection line connecting a midpoint of the first connection line to one of the one or more anatomical structures;
obtaining a normal of a plane that is determined by the first connection line and the second connection line; and
obtaining the orientation of the object according to the normal of the plane;
determine an optimal orientation for the object based on the original ultrasonic three-dimensional volume data;
compare the orientation of the object with the optimal orientation to obtain a rotation transformation parameter in a three-dimensional coordinate system;
perform a rotation transformation on the original ultrasonic three-dimensional volume data according to the rotation transformation parameter to obtain a transformed three-dimensional volume data, wherein when the object is a fetal face, the rotation transformation on the original ultrasonic three-dimensional volume data automatically rotates the fetal face such that a user can observe the fetal face;
detect a position of the object from the original ultrasonic three-dimensional volume data according to the image characteristic of the object;
determine a relative position of the object in a display window according to the position of the object;
compare the relative position of the object with a desired position of the object in the display window to obtain a displacement vector or a coordinate difference in the three-dimensional coordinate system; and
perform a coordinate transformation of the transformed three-dimensional volume data according to the displacement vector or the coordinate difference to translate the object to the desired position in the display window; and
output the transformed three-dimensional volume data to the display after the rotation transformation and the coordinate transformation to obtain an ultrasonic image.

* * * * *